US006615679B1

(12) United States Patent
Knollenberg et al.

(10) Patent No.: US 6,615,679 B1
(45) Date of Patent: Sep. 9, 2003

(54) ENSEMBLE MANIFOLD, SYSTEM AND METHOD FOR MONITORING PARTICLES IN CLEAN ENVIRONMENTS

(75) Inventors: Brian A. Knollenberg, Superior, CO (US); Glenn W. Brandon, Niwot, CO (US); Bryan Bast, Pittsburgh, PA (US)

(73) Assignee: Particle Measuring Systems, Inc., Boulder, CO (US)

( * ) Notice: Subject to any disclaimer, the term of this patent is extended or adjusted under 35 U.S.C. 154(b) by 0 days.

(21) Appl. No.: 09/638,366

(22) Filed: Aug. 15, 2000

(51) Int. Cl.[7] .......................... H01L 21/66; G01N 1/14; G01N 1/24
(52) U.S. Cl. .................. 73/863.33; 73/28.01; 73/61.71; 73/863.03; 73/864.34; 438/14
(58) Field of Search .................. 73/863.33, 863.03, 73/864.34, 28.01, 61.71, 31.02; 438/14

(56) References Cited

U.S. PATENT DOCUMENTS

| 3,357,257 A | * | 12/1967 | Herndon et al. ......... 73/863.33 |
| 3,643,689 A | | 2/1972 | Isreeli et al. ................ 137/561 |
| 3,765,247 A | * | 10/1973 | Riggs ....................... 73/863.33 |
| 4,113,434 A | | 9/1978 | Tanaka et al. ............. 422/94 X |
| 4,601,211 A | * | 7/1986 | Whistler ................... 73/863.33 |
| 4,860,598 A | * | 8/1989 | Bailey et al. ............. 73/863.33 |
| 4,993,271 A | * | 2/1991 | Vargason ............. 73/863.33 X |
| 5,005,430 A | * | 4/1991 | Kibler et al. ........ 73/863.33 X |
| 5,090,257 A | * | 2/1992 | Bruce .................. 73/864.34 X |
| 5,553,496 A | | 9/1996 | Nishiyama et al. ........ 73/432.1 |
| 5,553,507 A | * | 9/1996 | Basch et al. ......... 73/863.25 X |
| 5,601,234 A | | 2/1997 | Larue ............................. 239/1 |
| 5,856,623 A | | 1/1999 | Ahn et al. ................ 73/863.03 |
| 6,230,080 B1 | * | 5/2001 | Lee et al. .................... 700/275 |
| 6,234,005 B1 | * | 5/2001 | Han et al. .................... 73/38 X |
| 6,425,297 B1 | * | 7/2002 | Sharp ....................... 73/863.33 |

FOREIGN PATENT DOCUMENTS

| CA | 646702 | * | 8/1962 | ............. 73/863.33 |
| CH | 442807 | * | 1/1968 | ............. 73/863.33 |
| DE | 53334 | * | 1/1967 | ............. 73/863.33 |
| DE | 2013682 | * | 10/1971 | ............. 73/863.33 |
| JP | 60-200145 | * | 10/1985 | ............. 73/863.33 |
| SU | 215591 | * | 7/1968 | ............. 73/863.33 |

OTHER PUBLICATIONS

Andrew Benton, "Programmable gas sample selector" *Kent Tech. Rev.* (GB) No. 25, pp. 12–13, Jul. 1979 TDB–Acc–No. NN 9311217 "Environmental Monitoring and Control System for Clean Room Heating, Ventilation, and Air Conditioning Systems" *IBM Technical Disclosure Bulletin, US* vol. 36, No. 11, pp. 217–218 Nov. 1993.*

\* cited by examiner

*Primary Examiner*—Thomas P. Noland
(74) *Attorney, Agent, or Firm*—Patton Boggs LLP

(57) ABSTRACT

A system for detecting particles in a clean environment includes and ensemble manifold having a plurality of sample ports, a delivery port, and flow junction having no open-close valves or other flow selectors connecting all of said sample ports to said delivery port. In one embodiment, the ensemble manifold is mounted directly on a particle detector using a snap-on connector. A plurality of fluid sources are located in a clean environment, each of the fluid sources fluidically connected to one of the sample ports.

7 Claims, 7 Drawing Sheets

ENSEMBLE MANIFOLD, SYSTEM AND METHOD FOR MONITORING PARTICLES IN CLEAN ENVIRONMENTS

BACKGROUND OF THE INVENTION

1. Field of the Invention

The field of the invention relates to apparati and methods for monitoring particles in clean environments of the integrated circuit, electronic, pharmaceutical and other industries.

2. Statement of the Problem

The semiconductor and data storage industries are moving away from ballroom cleanrooms with exposed process environments toward enclosed process tools with autonomous air handling systems. Each process tool may be viewed as comprising a mini-environment, in which one or several process functions are performed. A mini-environment-based process tool may contain one or more than one clean-zone, each clean-zone incorporating separate filtration services and product handling systems. Thus, a modern integrated circuit manufacturing plant, commonly known as a fab, typically contains hundreds of smaller, miniaturized mini-environments. Mini-environments exist in a wide range of sizes, a typical size having a volume of 3 m×3 m×3 m. Because the air handling systems of a mini environment are close to the product, extremely isolated contamination events occur. Contamination is often not constant rather it may be a result of a process event. Thus, contamination events may be spatially or chronologically isolated. One of the serious problems of the integrated circuit manufacturing industry, as well as other industries requiring very clean environments, is the detection of these isolated events.

In typical fabrication sequences, front-opening-unified pods (FOUPs) carry wafers to the many mini-environments, robotics transfer wafers from the FOUPs to a manufacturing process zone, and after processing, the wafers return to the FOUPs. Data from mini-environments show that they are not as clean as initially imagined. Consequently, a mini-environment requires particle monitoring, and indirect air handling and compartmentalized nature of the mini-environment necessitates a particle counter with small dimensions and high probability of detecting an isolated particle event.

There are several basic methods known in the art for monitoring a mini-environments. The first is to use a dedicated sensor for each mini-environment to do continuous monitoring. A second technique is to use a multiplexed system, including a stepping manifold system and a single particle detector. With this technique, samples are drawn continuously from numerous mini-environments or from multiple points in a single mini-environment and are measured sequentially in steps a single sample at a time. A third, non-automated method uses a mobile sensor that is moved from one mini-environment to another. The sensor is attached to a "particle port" on the mini-environment.

FIG. 1 shows a diagrammatic sketch of a dedicated sensor system 100 as known in the art. A process tool 102 includes an enclosed gaseous mini-environment 104, which is being monitored for use of a sampling probe 106 which is connected by sampling to 108 to particle detector 110. A dedicated sensor, provides the obvious advantage that it continuously monitors the sampling zone of the sample probe, capturing brief intermittent events. A serious disadvantage, however, is that the sampling zone of a dedicated sensor is relatively small, typically having a footprint less than one square foot. A dedicated sensor, therefore, provides limited spatial coverage, detecting particles only in the sampling zone, and not in the other locations of the mini-environment. For example, a diagram of a process tool 202 is depicted in FIG. 2 containing a mini-environment 204 and four process functions 206, 208, 210, 212. The movement of a semiconductor wafer 214 through process tool 202 includes travel through zones designated by dashed area 220, including the liquid environments of process functions 206, 208, 210. Movement through the process tool 202 also includes travel through a gaseous clean zones along the path designated by arrows 230. A 12-inch wafer has a surface area of 0.8 sq. ft. If the exposed path through the gaseous mini-environment of the process tool is 24 feet, then the effective exposed area for the wafer is 19 sq. ft. A particle contamination event is generally localized to an area corresponding to 1 square foot or less. Thus, a dedicated sensor located at a single point along the 24-foot exposed process path 230 would detect a contamination event only if the event occurred within several inches of the location of the sampling probe. It is, however, economically and sometimes physically impractical to provides a large number of dedicated sampling probes and corresponding expensive particle counters to monitor continuously the entire process path of a process tool.

In a multiplexed monitoring system, a number of sampling probes are connected to a multiplexed stepping manifold. A diagrammatic sketch of the multiplexed monitoring system 300 is depicted in FIG. 3. Typically, fluid is drawn from each sample point 302 continuously through the multiplexing stepping manifold 310 by pump 350. In sequence, the manifold controller 312 selects a single sample 320 that is tested by the particle detector 330, while all other fluid flow from the unselected samples is discarded in the exhaust system 340. A multiplexed, stepping manifold system 300 allows monitoring of many locations using a single particle detector. A multiplexed system has a disadvantage, however, that a contamination event may go undetected for a relatively long time until the sample from the probe location reaches its turn in the multiplexing sequence. Indeed, a brief or intermittent contamination event may go completely undetected if its occurrence does not coincide with the timing of the multiplexing sequence. In a variation, referred to as a mixed-fluid manifold technique, two particle detectors are connected to each stepping manifold. A single sample is selected by the manifold and sent to one particle detector, as in a basic system, while the samples from all the other sample probes are combined and sent as a mixture to the second particle detector. In this manner, each sample probe location is monitored individually in sequence, while a combined mixed-fluid stream of all of the remaining samples is monitored continuously. This technique is expensive, however, because it requires two particle detectors and an expensive multiplexed stepping manifold with extra controls.

Conventional monitoring systems using stepping manifolds to monitor a mini-environment at a number of sample points typically draw a large volume of the air, sometimes greater than 1 cubic foot, from each sample point. This may adversely affect the whole fluid environment. The tubing leading to the probes takes up limited space in the process tool. When there are many sampling points to be monitored, it may be impossible to provide access for tubing to all of the sampling probes. Particles in the tubing, especially aerosol particles, may settle in the tubing, leading to false negative or low measurements and to clogging of the tubing. The stepping manifolds used in conventional techniques typically way on the order of 20 pounds, and occupy a large volume of space, having a diameter of a foot or more.

The mobile system has the advantage of having the lowest capital cost. But, it has the disadvantage of increased manpower costs and has a very low duty cycle.

The problems described above with respect to monitoring clean gaseous environments are also encountered in regard to maintaining clean liquid environments.

The integrated circuit manufacturing industry, as well as other industries requiring clean environments, needs a particle monitoring system that monitors and detects contamination events in a clean environment, providing good spatial coverage without significant gaps in time, in a manner that is economically and physically feasible.

Solution

The invention described in this specification provides an ensemble manifold, a system and a method that alleviate the problems described above.

An ensemble manifold in accordance with the invention combines all of the fluid samples collected in a clean environment and provides this ensemble flow to a particle detector. An ensemble manifold comprises: a plurality of sample ports; a delivery port adapted for fluidic connection to a particle detector; and a flow junction located between the sample ports and the delivery port, in which fluids flowing through the sample ports are combined.

In another aspect, an ensemble manifold comprises: a plurality of sample ports; a flow cell of a particle detector, in which fluids flowing through the sample ports are combined; and an outlet port.

A system in accordance with the invention for detecting particles in a clean environment comprises: an ensemble manifold having a plurality of sample ports and a delivery port; a plurality of fluid sources located in the clean environment, each of the fluid sources fluidically connected to one of the sample ports; a particle detector, the particle detector fluidically connected to the delivery port of the ensemble manifold. An embodiment of a system in accordance with the invention comprises a plurality of sampling probes in fluidic contact with the fluid sources, each sampling probe fluidically connected to one of the sample ports. Preferably, the sampling probes are isokinetic sampling probes. Typically, the clean environment is a mini-environment of a semiconductor wafer process tool. Fluid samples may be drawn from the clean environment into an ensemble manifold using house vacuum or vacuum pump or other suitable means. In a preferred embodiment, a system comprises a plurality of sample tubes, one end of each sample tube attached to one of the sampling probes, and the other end of the sample tube attached to one of the sample ports. Preferably an ensemble manifold comprises a special manifold adaptation designed for direct mounting of the ensemble manifold onto a selected particle detector. In another embodiment, a system may comprise a delivery tube for connecting the outlet (delivery port) or the ensemble manifold to the particle detector. The delivery tube has two ends, one end of the delivery tube attached to the delivery port of the ensemble manifold, and the other end of the delivery tube attached to the particle detector.

A method in accordance with the invention for detecting particles in a clean environment comprises steps of: continuously simultaneously drawing a plurality of fluid samples at a plurality of sample points in the clean environment; continuously combining the plurality of the fluid samples into a combined fluid stream (ensemble flow); continuously flowing the combined fluid stream into a particle detector; and then monitoring the combined fluid stream with a particle detector. Typically, each of the fluid samples is drawn through one of a plurality of sampling probes located at the plurality of sampling points, each of the sampling probes fluidically connected to one of the sample ports. Preferably, the drawing of fluid samples is conducted isokinetically. For this reason, the sampling probes preferably are isokinetic sampling probes. Preferably, the clean environment is a mini-environment of a semiconductor wafer process tool. A method in accordance with the invention is useful when the fluid samples comprise gaseous fluid and the particles are aerosol particles. A method in accordance with the invention is also useful when the fluid samples comprise liquid fluid.

DETAILED DESCRIPTION OF THE PREFERRED EMBODIMENT

1. Overview

Figure 6:
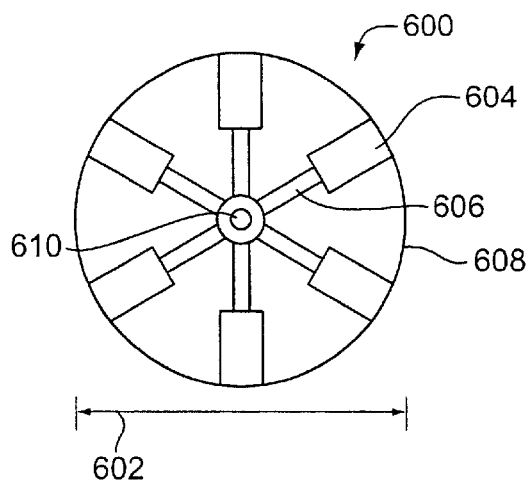
FIGS. 6, 7 and 8 depict scaled views of an exemplary ensemble manifold in accordance with the invention.
Figure 7:
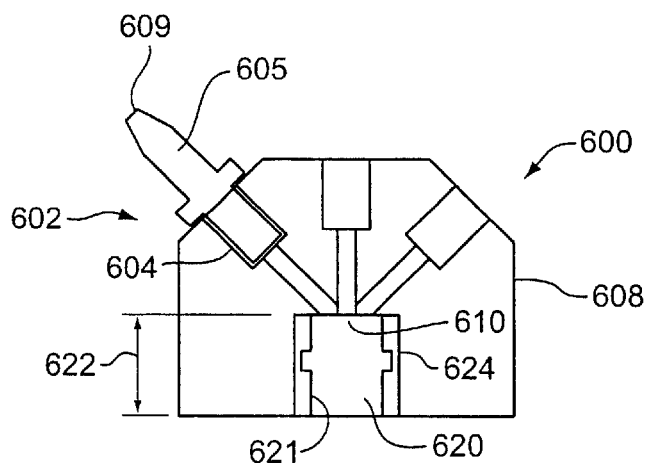
Figure 8:
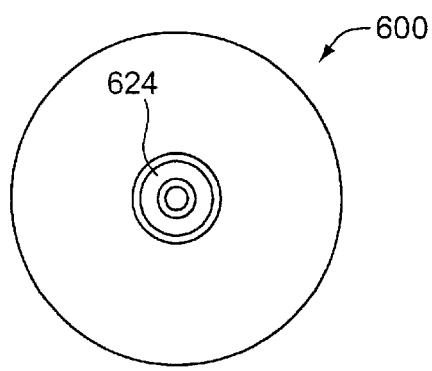

The invention is described below with the aid of FIGS. 4–9. It should be understood that FIGS. 4 and 5 do not represent any particular ensemble manifold or particle detection system. An ensemble manifold, a particle detection system and a method in accordance with the invention may be embodied in many variations that do not depart essentially from the embodiments described herein. It should be further understood that FIGS. 6–8 are only examples of an ensemble manifold in accordance with the invention, and these figures, as FIGS. 4 and 5, do not limit the scope of the invention, which is defined by the claims below.

The term "ensemble manifold" is used to distinguish a manifold device in accordance with the invention from other manifolds known in the art. An ensemble manifold in accordance with the invention has a plurality of inlet sample ports, a junction in which the sample fluids from all of the sample sources are combined, and an outlet or delivery port through which the combined sample stream flows to a particle detector. For all practical purposes, an ensemble manifold in accordance with the invention has no moving parts. In contrast with manifolds used in particle detection systems of the prior art, an ensemble manifold typically does not include open-close valves, flow selector mechanisms and switching mechanisms. Furthermore, an ensemble manifold requires no control apparatus to control the timing and switching of valves. As a result, an ensemble manifold in accordance with the invention is physically just a small fraction of the size of a conventional stepping manifold. Also, the capital cost of an ensemble manifold is a small fraction of the cost of a stepping manifold. An ensemble manifold is virtually maintenance-free.

The term "ensemble flow" refers to the combined flow of fluid samples from an ensemble manifold to a particle detector. The term "ensemble flow" is used to distinguish from the flow being measured in conventional systems, which do not measure simultaneously all of the fluid samples flowing into the manifold.

The term "direct connection" and "direct fluidic connection" and similar terms are used herein with reference to the connection an ensemble manifold to a particle detector. The terms indicate that a preferred embodiment of an ensemble manifold in accordance with the invention can be fluidically connected to a particle detector without intervening tubing. The term "directly on" or "mounted directly on" or similar terms are used herein with reference to the embodiment of the invention in which an ensemble manifold is directly connected to and supported by a particle detector. This is in contrast to prior art systems in which both the particle detector and other components of a mini-environment were individually and separately supported by a support framework or housing should be understood, however, that an ensemble manifold in accordance with the invention may be used in particular applications in which a separate adapting means is employed to connect the delivery port of an ensemble manifold to the inlet of a particle detector.

There is virtually no theoretical limit on the number of sample ports with which an ensemble manifold in accordance with the invention may be designed and operated. Similarly, a system and a method in accordance with the invention may include as few as two fluid sources for monitoring, or it may include up to multiples of ten fluid sample sources for flowing through an ensemble manifold into a particle detector.

2. Detailed Description

Figure 1:
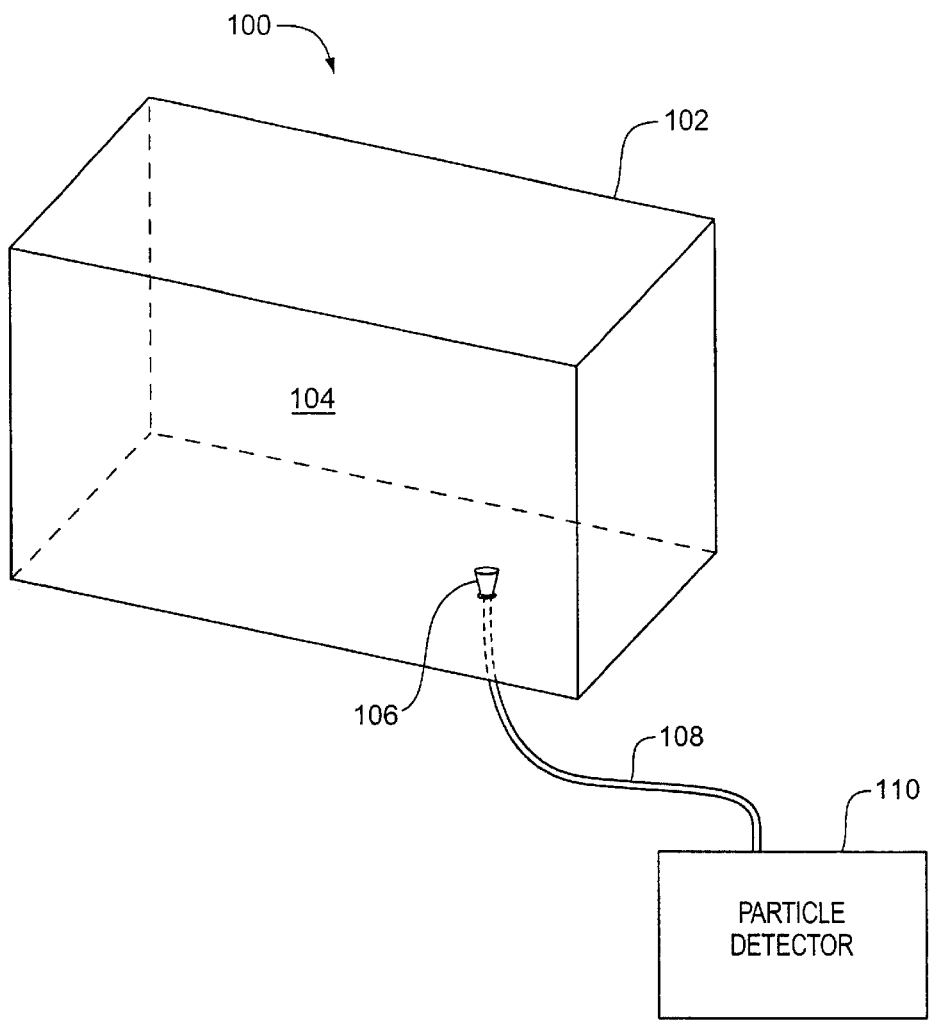
FIG. 1 shows a diagrammatic sketch of a dedicated sensor system as known in the art.
Figure 2:
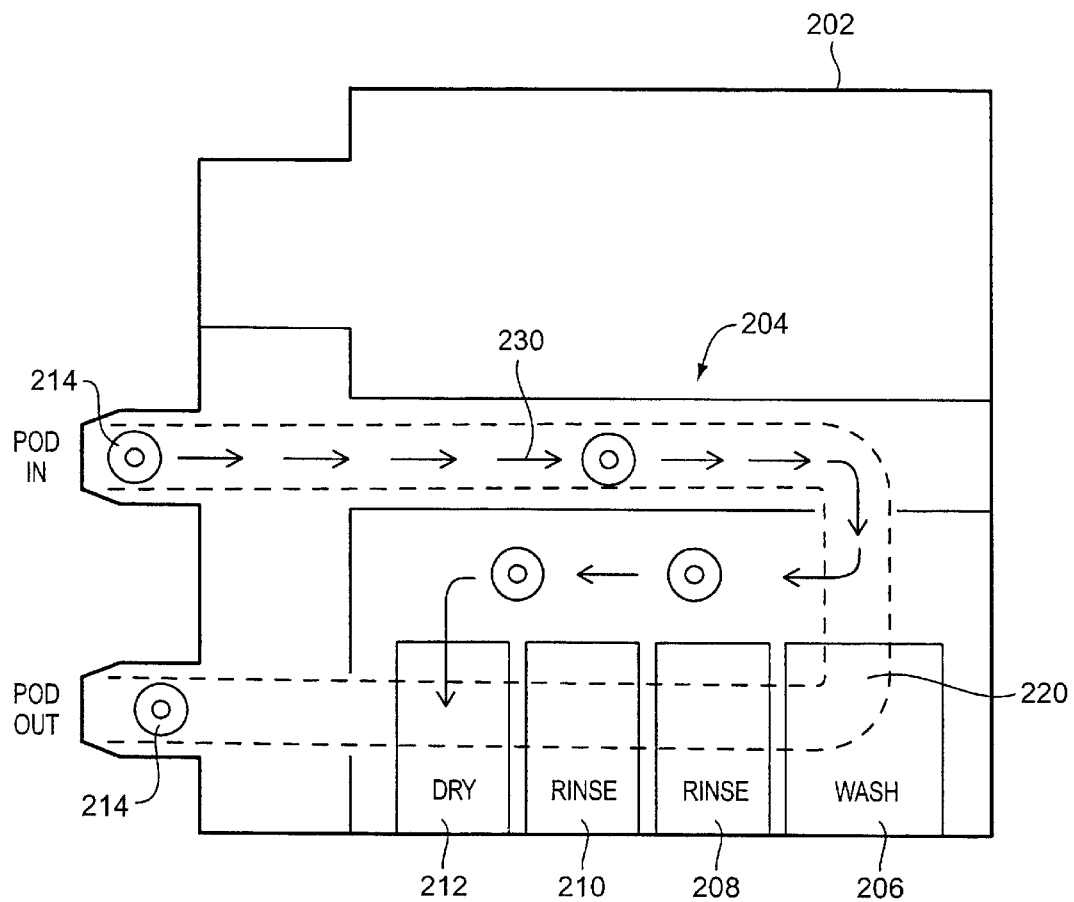
FIG. 2 shows a diagram of a prior art process tool containing a mini-environment, process functions, and a long process path in which brief intermittent contamination events remain undetected.
Figure 3:
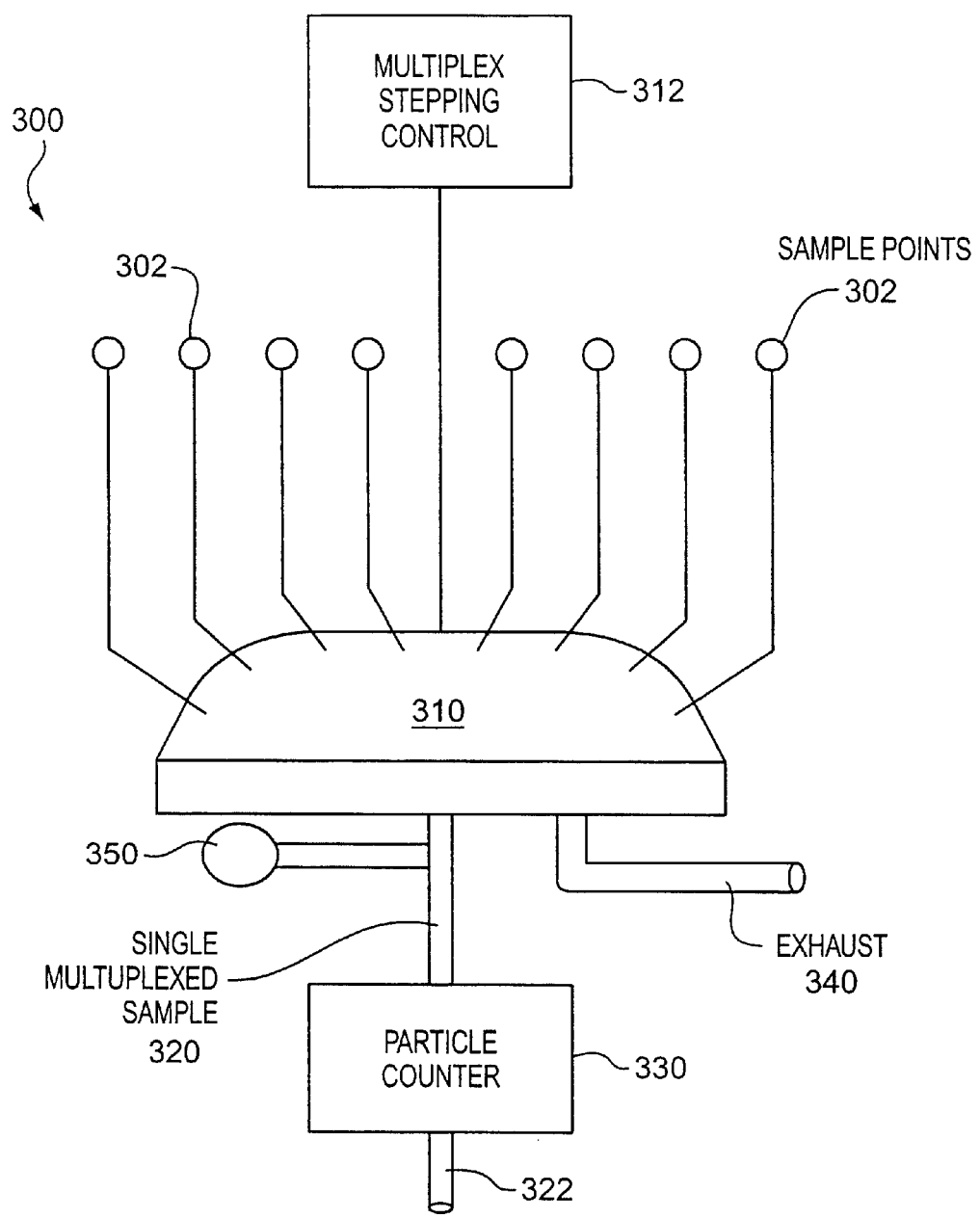
FIG. 3 depicts a diagrammatic sketch of a prior art multiplexed monitoring system using a stepping manifold.
Figure 4:
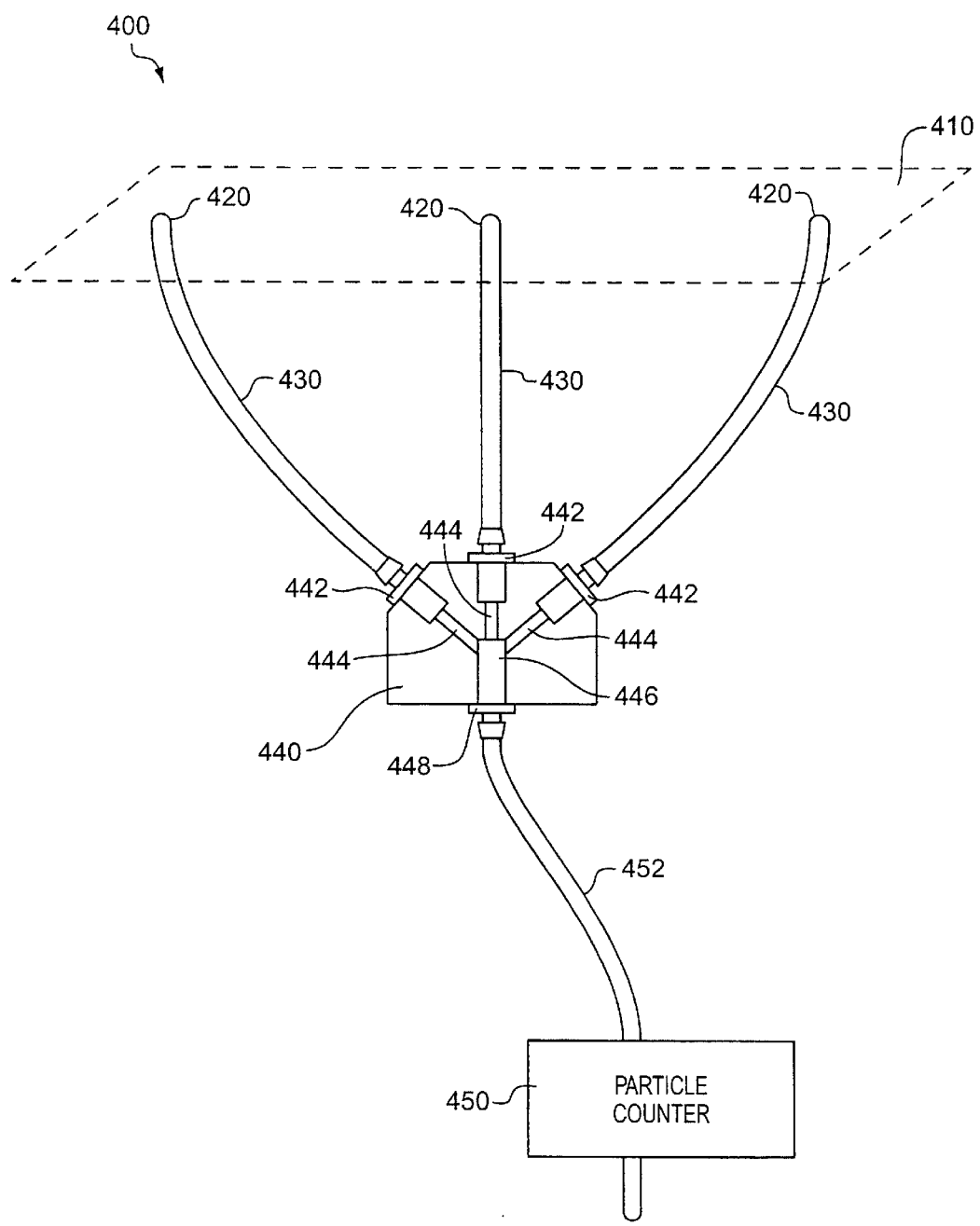
FIG. 4 depicted a system in accordance with the invention for detecting particles in a clean environment.

FIG. 4 shows a system 400 for detecting particles in a clean environment 410. A clean environment 410, typically a mini-environment in a process tool, includes fluid sample sources 420. Fluid samples flow through sample tubes 430 into ensemble manifold 440 through a plurality of sample ports 442. The fluids flowing through sample ports 442 continue flowing through inlet channels 444 and combine in flow junction 446. The resulting combined fluid stream flows through delivery port 448 to particle detector 450 via delivery tube 452. After measurement in particle detector 450, the fluid stream exits through exhaust system 460.

Figures 5A, 5B:
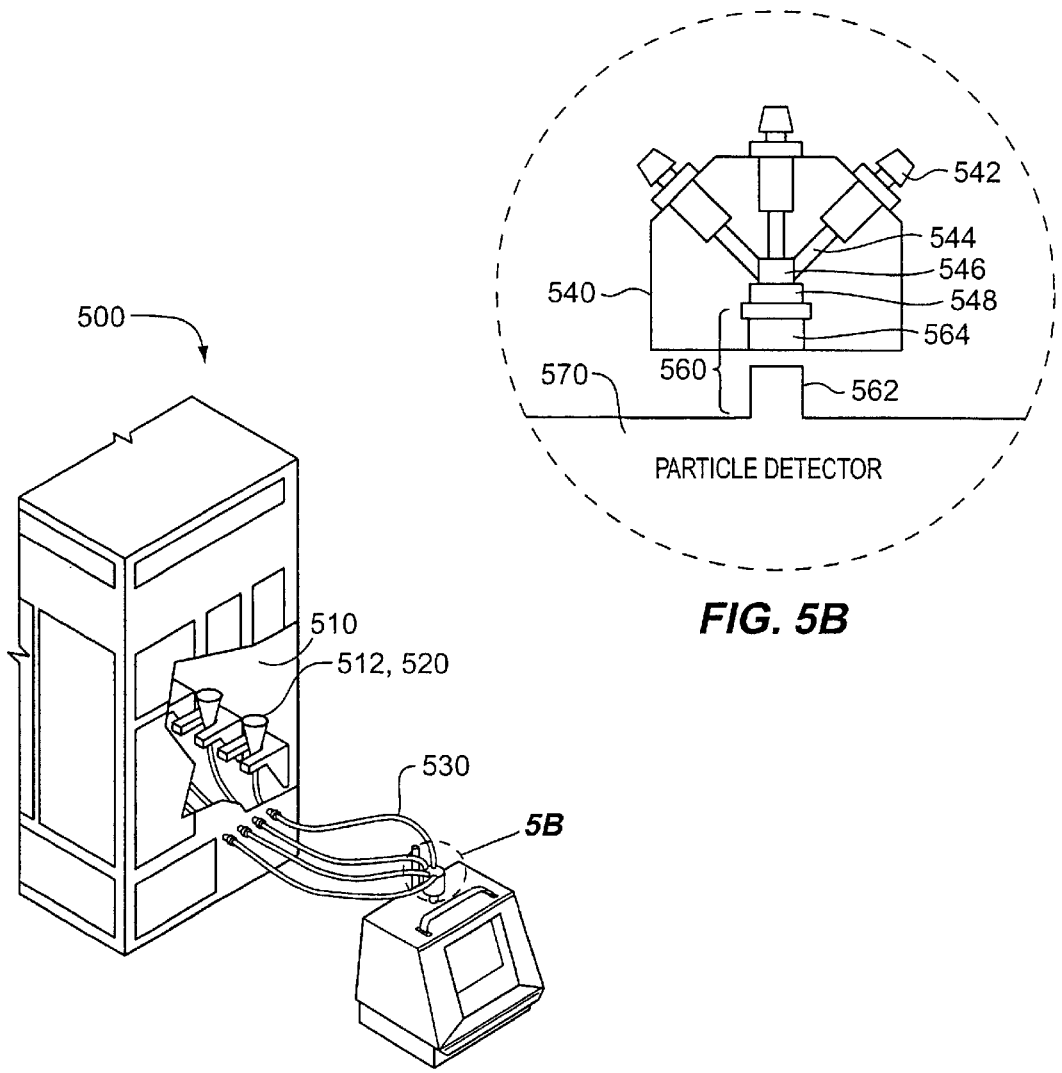
FIG. 5 depicts a preferred embodiment of an ensemble manifold and a system in accordance with the invention.

FIG. 5 depicts a preferred embodiment of an ensemble manifold and a system in accordance with the invention. A clean environment 510, typically a mini-environment, includes a plurality of sampling points 512. A plurality of sampling probes 520, preferably isokinetic sampling probes ("ISPs"), correspond to sampling points 512. Fluid samples are drawn essentially continuously from sample points 512 through sampling probes 520. The fluid samples may be drawn through sampling probes 520 by a variety of techniques, which may include house vacuum, a vacuum pump, or other means depending on whether fluid samples are liquid or gaseous and on numerous process variables. The plurality of fluid samples flow from sample probes 520 through sample tubes 530 into ensemble manifold 540 through a corresponding plurality of sample ports 542. In a preferred embodiment, sample tubes 530 are flexible plastic. The size of the tubing may vary depending on the volumetric flowrate of the fluid sample being drawn through each sampling probe 520. The flexibility of the tubing and its small diameter (typically not exceeding ¼ inch ID) makes it possible to provide access to a large number of sample tubes in and around the process tool. Thus, samples from a large number of sample points can be collected through a large number of sampling probes 520 and flowed through sample tubes 530 to ensemble manifold 540. Also, the small diameter of the sample tubing maintains fluid velocity in the sample tubes, thereby minimizing particle settling in the sample tubes. Connection of the ends of sample tubes 530 to sampling probes 520 and to sample ports 542 may be by various connectors and other means known in the art. As described below, a preferred means of connection is a pressure seal formed by tight contact between the inside walls of the tubing and beveled ends of the sampling probes 520 and sample ports 542. Ensemble manifold 540 is itself relatively small compared to stepping manifolds used in the prior art. As described in an example below, an ensemble manifold having seven sample ports 542 may have an outside diameter of 1.5 inches and a height of about an inch. Because manifold 540 is relatively small in size and light in weight, manifold adapter 560 allows manifold 540 to be mounted directly onto particle detector 570. In most applications, an ensemble manifold in accordance with the invention has a diameter not exceeding 3 in. and a similar height dimension preferably an assemble manifold weights less than 2 pounds. Typically an assemble manifold does not exceed ½ pound in weight; typically it occupies a total volume less than 14 cubic inches. Manifold 540 typically is mounted to the top panel of particle detector 570, creating a "pinhead" appearance, as depicted in FIG. 5. Fluidic connection between ensemble manifold 540 and particle detector 570 is effected by delivery connector 560, comprising male-end detector inlet port 562 and female-end 564. In a preferred embodiment as in FIG. 5, female-end 564 is integrated within delivery port 548. It should be understood, however, that fluidic connection between ensemble manifold 540 and particle detector 570 may be effected in accordance with the invention using one of numerous, different types of connection techniques and apparati. Preferably, it is connected with a quick-connect, snap-on connector 560. As known in the connector art, such connectors use resilient members which snap into place when the ensemble manifold is pressed onto the particle detector.

System 500 thereby provides several advantages over the prior art. The small-diameter flexible tubing allows convenient access to a large number of sampling points 512 in clean environment 510. A small-diameter tubing maintains flow velocity, thereby minimizing particles settling. Ensemble manifold 540 is small and light and inexpensive compared with stepping manifolds of the prior art. By means of a variety of customized adaptations of the manifold, ensemble manifold 540 may be quickly, directly and conveniently attached to a variety of different types of particle detectors. An ensemble manifold 540 may be designed and manufactured quickly and inexpensively to have an arbitrary number of sample ports 542. An ensemble manifold in accordance with the invention preferably contain no open-close valves, flow selectors or switching mechanisms used during normal operation (although some shut down or shunting mechanisms are typically used to shut down the particle detection system). Although embodiments of ensemble manifold 440 (FIG. 4) typically comprise sample ports 442 and inlet channels 444 having identical diameters and lengths, these need not be uniform. For example, the inside diameter of a particular inlet channel may be designed to be substantially larger than other inlet channels to reduce flow resistance through that channel, and thereby to increase the relative size of the fluid sample flowing through the channel. In this manner, the fluid sample drawn from a selected sample point in a clean environment may be increased relative to others to increase the overall sensitivity of the particle detection system towards the selected point.

EXAMPLE 1

FIGS. 6, 7 and 8 depict scaled views of an exemplary ensemble manifold in accordance with the invention. FIG. 6 is a top view of the ensemble manifold 600 having seven sample ports and one delivery port. FIG. 7 is a cross-section view of ensemble manifold 600. FIG. 8 is a bottom view. Ensemble manifold 600 is suitable for combining seven fluid samples sampled continuously at a flowrate of approximately 1/7 cu. ft. per minute, which are combined to form a combined flow stream of approximately 1 cu. ft. per minute. Dimension 602 representing the outside diameter of ensemble manifold 600 has value of 1.5 inches. Sample ports 602 comprise sample port holes 604 and barb fittings 605. Sample port holes 604 are made with a 0.25–28 standard tap with a depth of 0.325 in. Inlet channels 606 have a diameter of 0.094 inches and a depth of 0.80 inches, measured from the outside diameter surface 608. The barbed end 609 of barbed sitting 605 is inserted into the end of a plastic sample tube to effect fluidic connection. As depicted in FIGS. 6 and 7, inlet channels 606 converge at flow junction 610, at which fluid samples combine during operation to form a combined fluid stream (ensemble flow). Preferably, ensemble manifold 600 is made of nickel-plated aluminum, though other suitable materials known in the art may be used.

Ensemble manifold 600 of FIGS. 6 and 7 is directly mountable to a particle detector by means of a customized delivery port 620, specially adaptable to virtually any particle detector. Exemplary ensemble manifold 600 was specially adapted for fluidically connecting and mounting to an aerosol particle detector, Model Airnet, 1.0 CFM (cubic feet per minute), commercially available from Particle Measuring Systems, Inc. ("PMS"), of Boulder, Colo. In exemplary ensemble manifold 600 of FIG. 6 and FIG. 7, delivery port 620 functions as the receptor for the inlet port of the Airnet particle detector, which is inserted into the delivery port 620 to effect fluidic connection between ensemble manifold 600 and the Airnet detector. The inside diameter dimension of the hole 624 at the bottom of ensemble manifold 600 (see FIG. 8), bounded by cylindrical surface 621 of FIG. 7, is 0.342 inches.

EXAMPLE 2

An ensemble manifold, a system and a method in accordance with the invention were utilized to monitor aerosol particles present in the wafer-sorter of a 300 mm fab. Seven ISP sampling probes were mounted using conventional methods in the process tool. One of the seven probes was located centrally in the many-environment of the tool, the other probes were located at each of the load ports and wafer transfer mechanisms. Seven flexible plastic sampling tubes having an inside diameter of 1/8 inch connected the sampling probes with seven corresponding sample ports of an ensemble manifold similar to the one described in Example 1. Fluid samples were drawn simultaneously and continuously through the seven sampling ports at a flowrate of 1/7 cfm, and were combined in the ensemble manifold in a combined flow stream of 1.0 cfm. The combined flow stream from the ensemble manifold was analyzed and measured by a particle detector, a PMS model Airnet, 1.0 CFM aerosol particle detector.

A dedicated system comprising a single sampling probe and a dedicated particle counter measured a single fluid sample drawn continuously at a flowrate of 1.0 CFM. The single probe was installed at the same central location in the tool as mentioned above.

Figure 9:
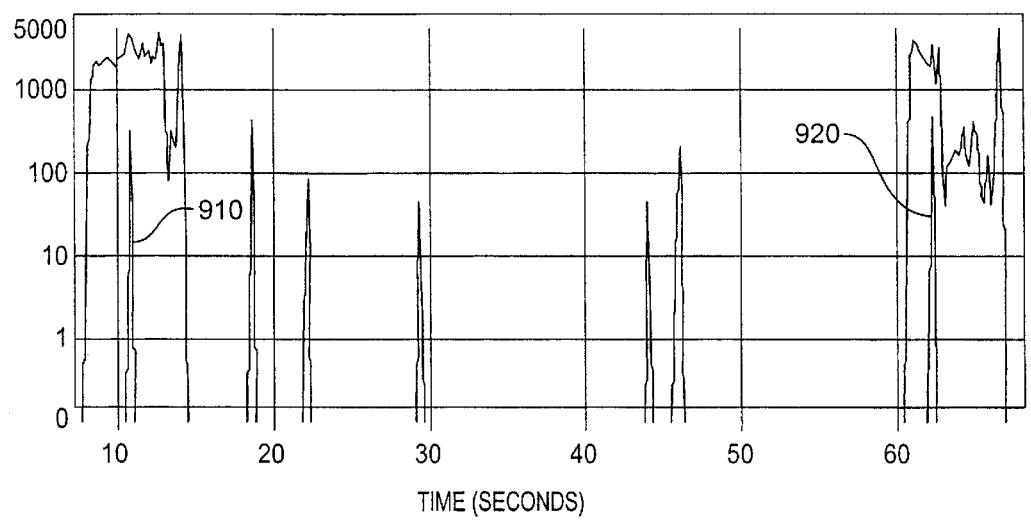
FIG. 9 is a graph in which the normalized particle counts of particle counting measurements from a conventional dedicated system and from a system in accordance with the invention are plotted as a function of time in minutes.

The results of the particle counting measurements from the dedicated system and from the system in accordance with the invention are plotted on the graph of FIG. 9. In the graph of FIG. 9, normalized particle counts are plotted as a function of time in minutes. The dedicated sensor detected only two brief contamination events, represented in FIG. 9 by peak 910 and peak 920. Peak 910 occurred at about 11 minutes, and peak 920 occurred at about 62 minutes. In contrast, the exemplary system and method in accordance with the invention detected contamination events beginning at 7, 18, 22, 29, 44, 46, and 61 minutes. The particle counts detected in accordance with the invention during the events beginning at 7 and 61 minutes were very large compared to the events detected by the dedicated sensor. The exemplary results presented in FIG. 9 demonstrate the utility of a method and a system in accordance with the invention.

A feature of the invention is that it recognizes that when contamination is present in an part of a micro-environment or other clean environment operation of the systems in the environment is not desirable. That is, prior art systems used complex switches etc. to try to determine precisely where a contamination was occurring. However, in actual practice, when any contamination occurs, the system is taken off-line until the contamination is corrected. Generally, during the down time, the system is inspected using conventional methods. Thus, when used in combination with the general practices in the art, the system according to the invention is both practical and efficient as well as being economical.

In an alternative embodiment of an ensemble manifold in accordance with the invention, the ensemble manifold includes a flow cell of a particle detector. For example, with reference to FIG. 4, a particle detection flow cell 460 may be located between flow junction 446 and delivery port 448. With this embodiment, particle detection of the combined flow stream is effected within the ensemble manifold itself, making it unnecessary to flow the combined flow samples from the outlet of the manifold to a separate particle detector unit.

There have been described what are at present considered to be the preferred embodiments of the invention. It will be understood that the invention can be embodied in other specific forms without departing from its spirit or essential characteristics. For example, while the invention has been described in terms of an air particle detection system, it also may be incorporated into water, chemical and other detection systems. Many other connectors and ports can be used in combination with the ensemble manifold. Further, now that the possibility and advantages of an ensemble manifold has been disclosed, many modifications and variations of the principles disclosed may be devised. The present embodiments are, therefore, to be considered as illustrative and not restrictive. The scope of the invention is indicated by the appended claims.

We claim:

1. A method for detecting particles comprising:
providing a mini-environment with a plurality of possible contamination event sources;
continuously simultaneously drawing each of a plurality of fluid samples from one of said possible contamination event sources in said mini-environment;
continuously combining all of said plurality of fluid samples into a combined fluid stream;

continuously flowing said combined fluid stream into a particle detector; and confining each said fluid sample within a separate enclosed region in between said drawing and said combining.

2. A method as in claim 1, wherein each of said fluid samples is drawn through one of a plurality of sampling probes located at said plurality of possible contamination event sources.

3. A method as in claim 1, wherein said drawing of fluid samples is conducted isokinetically.

4. A method as in claim 1, further comprising using a pump for drawing said fluid samples into said sampling probes.

5. A method as in claim 1, wherein said fluid samples comprise gaseous fluid.

6. A method as in claim 1, wherein said particles are aerosol particles.

7. A method as in claim 1, wherein said fluid samples comprise liquid fluid.

* * * * *

UNITED STATES PATENT AND TRADEMARK OFFICE
CERTIFICATE OF CORRECTION

PATENT NO.    : 6,615,679 B1  
DATED         : September 9, 2003  
INVENTOR(S)   : Brian A. Knollenberg, Glenn W. Grandon and Bryan Bast It is certified that error appears in the above-identified patent and that said Letters Patent is hereby corrected as shown below:

Title page,
Item [*] Notice, delete "Subject to any disclaimer, the term of this patent is extended or adjusted under 35 U.S.C. 154(b) by 0 days" and insert -- Subject to any disclaimer, the term of this patent is extended or adjusted under 35 U.S.C. 154(b) by 107 days --

Signed and Sealed this

Twenty-eighth Day of September, 2004

JON W. DUDAS
*Director of the United States Patent and Trademark Office*